United States Patent [19]

Raleigh et al.

[11] Patent Number: 5,447,997
[45] Date of Patent: Sep. 5, 1995

[54] SILICONE POLYETHER CARBOXYLIC ACIDS

[75] Inventors: William J. Raleigh, Rensselaer, N.Y.; James A. Campagna, Pittsfield, Mass.; Michael A. Lucarelli, Mattoon, Ill.

[73] Assignee: General Electric Company, Waterford, N.Y.

[21] Appl. No.: 212,610

[22] Filed: Mar. 11, 1994

[51] Int. Cl.$^6$ .......................................... C08F 283/12
[52] U.S. Cl. ...................................... 525/474; 528/26; 528/29; 528/15
[58] Field of Search ............................ 528/26, 29, 15; 525/474

[56] References Cited

U.S. PATENT DOCUMENTS

| | | |
|---|---|---|
| 3,182,076 | 5/1965 | Holdstock . |
| 3,220,972 | 11/1965 | Lamoreaux . |
| 3,336,239 | 8/1967 | Bailey . |
| 3,629,165 | 12/1971 | Holdstock . |
| 3,775,452 | 11/1973 | Karstedt . |
| 4,228,345 | 10/1980 | Stricker et al. . |
| 4,381,396 | 4/1983 | Ryang . |
| 4,442,903 | 12/1983 | Ashby . |
| 4,587,320 | 5/1986 | Swihart . |
| 4,683,271 | 7/1987 | Lin et al. . |
| 4,927,952 | 5/1990 | Gueyne et al. . |
| 4,937,277 | 6/1990 | O'Lenick, Jr. . |
| 5,248,783 | 9/1993 | O'Lenick . |
| 5,296,625 | 3/1994 | O'Lenick, Jr. et al. . |
| 4,946,818 | 8/1990 | Lewis . |
| 4,990,643 | 2/1991 | Traver . |
| 4,996,342 | 2/1991 | Ching et al. . |
| 5,189,190 | 2/1993 | Ching et al. . |

Primary Examiner—Melvyn I. Marquis

[57] ABSTRACT

A polyether silicone carboxylic acid or salt composition thereof useful for personal care applications.

10 Claims, No Drawings

SILICONE POLYETHER CARBOXYLIC ACIDS

FIELD OF THE INVENTION

The instant invention pertains to organosilicone polymers that have been functionalized by the presence of carboxylic acid groups. More particularly the instant invention pertains to a polyorganosilicone polycarboxylic acid. Additionally, the instant invention pertains to a method for conveniently preparing the polyorganosilicone polycarboxylic acids of the invention. Further the instant invention also pertains to the uses of these polyorganosilicone polycarboxylic acids in polymer and plastic formulations and in personal care formulations.

BACKGROUND OF THE INVENTION

This invention relates to a method of preparing carboxy functional silicones. More particularly this invention relates to a method for preparing carboxy functional silicones from a polyether silicone with an acid anhydride or halide.

Carboxy functional silicones are useful in many applications where water- and alcohol-soluble organopolysiloxanes are desirable. For example they are useful as emulsifying agents for the formation of aqueous emulsions of conventional organopolysiloxane fluids and in applications such as alcohol based cosmetics. Carboxy functional silicones can also function as reactants for the preparation of polysiloxane polyether copolymer surfactants which are useful additives in polyurethane foam.

Historically it has been difficult to prepare siloxanes or polyorganosiloxanes containing a carboxylic acid functionality. The synthesis of precursors to such carboxylic acid functional silicones such as nitriles and other acid precursors has been difficult. A previous approach that has been utilized without much success has been the hydrosilation of acrylonitrile using dichloromethylsilane or 3-butenenitrile and dichloromethylsilane.

In the art developed by Holdstock as taught in U.S. Pat. Nos. 3,182,076 and 3,629,165 carboxy functional silicones are prepared by hydrolysis and condensation of a mixture containing organotrichlorosilane, a diorganodichlorosilane, and a cyanoalkyldiorganochlorosilane. During the hydrolysis and condensation of these reactants, the various silicon bonded chlorine atoms are replaced by hydroxyl groups that intercondense to form siloxane linkages. The nitrile radical hydrolyzes to a carboxy radical. Hydrochloric acid is a by-product formed in the reaction and thus the reaction mixture is very corrosive.

Under the usual conditions of platinum catalysis of the hydrosilation reaction, the hydrosilation of nitriles to yield a cyanoalkylorganosilane is difficult. Subsequently a copper amine catalytic system was developed that facilitated the hydrosilation of nitriles. The synthesis of a carboxylic acid siloxane was achieved by the co-hydrolysis of acrylonitrile and 3-butenenitrile resulting in a siloxane having the following formula:

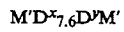

where M' represents the portion from 3-butenenitrile and D$^y$ represents the acrylonitrile adduct.

Another synthetic route for the production of a carboxylic acid adduct consists of reacting an unsaturated acid such as 10-undecenoic acid with trimethylchlorosilane to from the silyl ester followed by a catalytic hydrosilation. A subsequent hydrolysis of the hydrosilated trimethylchlorosilylester of unsaturated acid will yield the siloxy carboxylic acid derivative, as taught in U.S. Pat. No. 4,990,643 which is herewith incorporated by reference.

A similar reaction pathway that could be utilized to provide carboxy functionalized silicones is that taught by Ryang in U.S. Pat. No. 4,381,396, herewith incorporated by reference, wherein a hydride fluid is reacted with a norbornene carboxylic acid anhydride in the presence of a platinum hydrosilation catalyst to yield silicon functionalized norbornane mono-anhydrides or di-anhydrides. Ryang teaches the use of such compounds for the synthesis of organosilicon polyimide copolymers and polydiorganosiloxane polyimide block polymers and copolymers. However, a simple hydrolytic reaction of the mono- or di-anhydride should yield a carboxylic acid functionalized norbornylsiloxane or silicone. The use of norbornyl compounds is complicated by their well-known high levels of toxicity.

These approaches have significant drawbacks. The nitriles and norbornanes are toxic materials and require extensive precautions to avoid injury to personnel conducting the preparation of the siloxy derivative. The silyl ester has a very pronounced hydrolytic instability and thus requires elaborate steps to avoid contamination by water and a consequent premature hydrolysis of the ester. These drawbacks tend to inhibit the development of large scale processes for the production of silyl or siloxy carboxylic acids. A more convenient route to the preparation of such water soluble silicon containing carboxylic acids is desirable.

Carboxylic acid silicone derivatives were prepared via the addition of alcohol substituted siloxanes with dodecenyl succinic anhydride (DDSA) to produce the corresponding carboxylic acid adducts. The DDSA silicone adducts of the alcohol substituted siloxanes were, as synthesized, not water soluble. It is hypothesized that the hydrophobic nature of the silicone backbone overrides the hydrophilic contribution of the carboxylic acid functionality. Neutralization of the DDSA silicone adduct with potassium hydroxide resulted in the formation of a very viscous water-insoluble fluid.

Carboxylic acid silicone derivatives are desirable from the standpoint that these materials may be water soluble because of the acid functionality, that they may serve as emulsifying agents for less hydrophilic silicones, and therefor useful in personal care products.

SUMMARY OF THE INVENTION

The general preparation of silicon containing carboxylic acids of the instant invention herein described is summarized by the reaction of an unsaturated polyether with a siloxane containing silicon hydride to form a silicon carbinol or polyether silicone that is subsequently reacted with an acid anhydride or acid halide to yield a carboxylic acid functionalized silicone or siloxane derivative.

More particularly the instant invention pertains to a silicone polyether carboxylic acid comprising:

a) a polyether-silicone copolymer,

where $A^x$ represents a siloxy derivative selected from the group of silicone hydride compounds consisting of:
i) $TD_xM_3''$
ii) $TD_xD_y''M_3''$
iii) $TD_y''M_3''$
iv) $TD_xD_y''M_3$
v) $TD_y''M_3$
vi) $M''D_xD_y''M''$
vii) $M''D_xM''$
viii) $MD_y''M$
ix) $MD_xD_y''M$
x) $M''D_y''M''$
xi) $M''Q$
xii) $[D'']_z$ or any combination thereof wherein T represents a trifunctional siloxy group of the formula $RSiO_{3/2}$ with R being a saturated or unsaturated monovalent hydrocarbon radical, D represents a difunctional siloxy group of the formula $R_2SiO_{2/2}$, D" is a difunctional siloxy hydride of the formula $RHSiO_{2/2}$, M represents a monofunctional siloxy group of the formula $R_3SiO_{1/2}$ where each R is independently selected from the group of monovalent saturated or unsaturated hydrocarbon radicals; M" is a monofunctional siloxy hydride of the formula $R_2HSiO_{1/2}$, Q is a quadrifunctional siloxy group of the formula $SiO_{4/2}$; and $[D'']_z$ a cyclic oligomer of D" with z indicating the number of D" moieties forming the cyclic ring, with x greater than 1, y greater than 1 and z equal to or greater than 3 wherein p ranges from zero to about 500 and q ranges from about 1 to about 500, preferably p ranges from zero to about 100 and q ranges from about 1 to about 100, more preferably p ranges from one to about 20 and q ranges from about 1 to about 20, where $E^y$ is

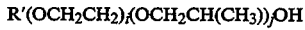

and where R' is an alkenyl or alkynyl group and i and j may vary from 0 to 50 such that the sum of i and j is at least one; and b) an acid anhydride or halide of a bi- or multi-functional organic carboxylic acid.

The instant invention also pertains to a polyether silicone intermediate necessary to the preparation of the polyether silicone carboxylic acid. The instant invention further pertains to the alkali metal and amine neutralization salts of said polyether silicone carboxylic acid, especially the salts of lithium, sodium, potassium, and organic ammonium ions. The instant invention still further pertains to the use of the polyether silicone carboxylic acids and salts thereof in personal care applications.

DETAILED DESCRIPTION OF THE INVENTION

The reaction of DDSA or other bi- or multi-functional organic acid derivative with a polyether silicone copolymer

where p may generally ranges from about 1 to about 50 and q may generally range from about 1 to about 10; and where $A^x$ is selected from the list of the following silicone hydride compounds:
i) $TD_xM_3''$
ii) $TD_xD_y''M_3''$
iii) $TD_y''M_3''$
iv) $TD_xD_y''M_3$
v) $TD_y''M_3$
vi) $M''D_xD_y''M''$
vii) $M''D_xM''$
viii) $MD_y''M$
ix) $MD_xD_y''M$
x) $M''D_y''M''$
xi) $M''Q$
xii) $[D'']_z$ or combinations of any of the forgoing wherein T represents a trifunctional siloxy group of the formula $RSiO_{3/2}$ with R being a saturated or unsaturated monovalent hydrocarbon radical, D represents a difunctional siloxy group of the formula $R_2SiO_{2/2}$, D" is a difunctional siloxy hydride of the formula $RHSiO_{2/2}$, M represents a monofunctional siloxy group of the formula $R_3SiO_{1/2}$ where each R is independently selected from the group of monovalent saturated or unsaturated hydrocarbon radicals; M" is a monofunctional siloxy hydride of the formula $R_2FISiO_{1/2}$, Q is a quadrifunctional siloxy group of the formula $SiO_{4/2}$; and $[D'']_z$ a cyclic oligomer of D" with z indicating the number of D" moieties forming the cyclic ring, with x greater than 1, y greater than 1 and z equal to or greater than 3; and $E^y$ is:

where R' is an alkenyl or alkynyl group and is preferably allyl, vinyl or actylenyl and more preferably allyl or vinyl, i and j may range from 0 to 50, such that the sum of i and j is at least one, produces a carboxylic acid functionalized polyorganosiloxane that may be rendered water soluble when neutralized, preferably when neutralized with sodium, potassium, or other alkali metal.

The reaction may be generally characterized by the following reaction scheme: I. an organic acid anhydride or organic acid halide is reacted with, II. a hydroxy functionalized polyether silicone or siloxane to yield, III. a polyether silicone polymer or copolymer carboxylic acid; and optionally, IV. neutralization comprising the use of an alkali metal, especially the salts of lithium, sodium, and potassium.

Specifically the hydroxy functionalized polyether silicone is prepared via a hydrosilation reaction with an unsaturated polyether. The silicone hydrides or parent silicones that become derivatized and incorporated into the polyether silicone and that are useful for the practice of the present invention are materials of the general formula:
i) $TD_xM_3''$
ii) $TD_xD_y''M_3''$
iii) $TD_y''M_3''$
iv) $TD_xD_y''M_3$
v) $TD_y''M_3$
vi) $M''D_xD_y''M''$
vii) $M''D_xM''$
viii) $MD_y''M$
ix) $MD_xD_y''M$
x) $M''D_y''M''$
xi) $M''Q$
xii) $[D'']_z$ or combinations of any of the forgoing wherein T represents a trifunctional siloxy group of the formula RSi- $O_{3/2}$ with R being a saturated or unsaturated monovalent hydrocarbon radical, D represents a difunctional siloxy group of the formula $R_2SiO_{2/2}$, D" is a difunctional siloxy hydride of the formula $RHSiO_{2/2}$, M represents a monofunctional siloxy group of the formula $R_3SiO_{1/2}$ where each R is independently selected from the group of monovalent saturated or unsaturated hydrocarbon radicals; M" is a monofunctional siloxy hydride of the formula $R_2HSiO_{1/2}$, Q is a quadrifunctional siloxy group of the formula $SiO_{4/2}$; and $[D"]_z$ a cyclic oligomer of D" with z indicating the number of D" moieties forming the cyclic ring, with x greater than 1, y greater than 1 and z equal to or greater than 3.

Any of the silicone hydrides listed above are reacted with an unsaturated polyether alcohol under conditions of hydrosilation to form a silicone carbinol or polyether silicone and are typically catalyzed by a platinum catalyst. Such catalysts are well-known in the art and are described in the following U.S. Pat. Nos. 3,775,452; 4,228,345; 3,336,239; 4,421,903; 3,220,972; and 4,946,818.

The silicone carbinol formed in the previous reaction step is then reacted with either an acid anhydride or the acid halide of a bifunctional or multi-functional organic carboxylic acid. A preferred acid anhydride is dodecenylsuccinic anhydride (DDSA), which is an alkyl substituted succinic anhydride. Other acid anhydrides or acid halides that may be used in the practice of this invention include but are not limited to phthalic anhydride, maleic anhydride or their corresponding acid halides. The cyclic acid anhydrides form a class of preferred anhydrides of carboxylic acids in the practice of this invention. Reaction of the silicon carbinol formed in the hydrosilation reaction with the acid anhydride or halide forms the carboxy or carboxylic acid functionalized silicone of the present invention. Multi-functional acid derivatives may be employed, it is sufficient that the one of the acid groups esterify the hydroxyl functionality of the silicon carbinol in order to yield the carboxy or carboxylic acid functionalized silicone of the present invention.

EXAMPLES

Example 1

To 36 g (0.62 moles) of allyl alcohol were added 5 g of 0.1 N sodium acetate iso-propanol buffer and 76 g of n-hexane. After an azeotropic distillation of approximately three hours, 0.1 ml of 0.1N sodium acetate, and a standard Pt hydrosilation catalyst reagent were added followed by the slow addition of 280 g (0.20 moles) of a hydride fluid, $TD15^{MH}$. During the following one hour reaction period an exothermic process raised the temperature of the reactants from 60° C. to 90° C., completion of the reaction was indicated by the disappearance of the infrared spectral band attributable to the presence of Si—H. 62 g of succinic anhydride dissolved in 200 ml of acetone were then added to the reaction mixture. Upon addition of the acetone solution, some of the anhydride precipitated and did not redissolve upon heating to reflux temperature. The solvents were distilled away from the reactants and the neat mixture was heated to 140° C., at which temperature reaction did occur as indicated by the disappearance of the infrared spectral bands attributable to the anhydride and the simultaneously coalescence and overlap of two broad infrared spectral bands centered at 1730 cm$^{-1}$ (representing formation of the ester and carboxylic acid).

Example 2

212.5 g of a diallyl alcohol adduct, synthesized as per the procedure of example 1, and having the following structure:

was added to 207 g of n-hexane, followed by the addition of 0.22 g of toluene sulfonic acid. The reactants were heated to 50° C. and 138.5 g of DDSA dissolved in 75 g of hexane was added slowly. The extent of reaction was monitored by observing the intensity and gradual disappearance of the carbonyl bands in the infrared spectrum normally associated with the presence of DDSA, and attributable to DDSA as the only carbonyl bearing species present in the reaction mixture. Additionally the appearance of two new infrared spectral bands at 1735 cm$^{-1}$ and 1710 cm$^{-1}$ (representing formation of the ester and carboxylic acid). On the basis of these spectral observations, the reaction had not gone to completion after a four hour period at 70° C. An additional 0.1 g of the acid catalyst was added and the reaction was allowed to proceed an additional eight hours at 80° C. Infrared spectral analysis indicated that the reaction had gone to completion however, a small amount of excess DDSA starting material remained present. The reaction solvent was removed by rotoevaporation to yield 361.4 of an oil product. The oil product was insoluble both in water and in 1:5 by weight water:ethanol solution. 163.5 g (0.11 moles) of the oil were suspended in 100 g of water, to which was added 12.5 g (0.22 moles) of potassium hydroxide in 50 g water. Immediately upon addition of the aqueous base, a white oily precipitate formed and the entire mixture became extremely viscous. Subsequent addition of more water or the application of heat or both failed to render the viscous oil soluble to any measurable extent.

Example 3

68.9 g of a carboxylic fluid made according to the teachings of Holdstock) was suspended in 70 g of water. 11.6 g (0.20 moles) of potassium hydroxide in 25 g water was added to this suspension. The mixture behaved in the same fashion as the viscous insoluble oil of example 2.

Example 4

100 g of a polyether-silicone copolymer,

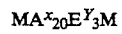

where $E^y$ is

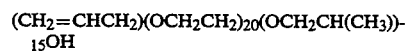

were dissolved in mineral spirits followed by the addition of 0.01 g of toluene sulfonic acid. The mixture was heated to 100° C. 11.2 g of DDSA in 100 g of mineral spirits was then added slowly. As in example 2, the reaction was monitored by following the appearance in the infrared of bands at 1740 cm$^{-1}$ and 1710 cm$^{-1}$ and the disappearance of the carbonyl infrared spectral bands attributable to the anhydride reactant. The solvent was removed. The resultant carboxylic acid silicone oil had a viscosity of 2700 centistokes and a flash point of 80° F.

In the following examples of surfactant preparation the preparative steps were as follows:

1) Dry the hydride fluid and the toluene solvent azeotropically under conditions of reflux distillation;
2) Cool the solution to a temperature below 100° C.;
3) Add anhydrous sodium acetate and the platinum catalyst solution;
4) Add slowly over the course of an hour a toluene solution of a polyether;
5) Raise the temperature to 100° C. and hold at temperature for five hours;
6) Remove the toluene solvent from the reaction mixture by a vacuum distillation at 10mm Hg pressure using a nitrogen purge; and
7) Filter to remove any contaminating solids.

Example 5

Surfactant A
Following the previously outlined procedure:
335 g of MDHM (mw=222) constituted the hydride fluid,
335 g of toluene solvent
0.2 g of anhydrous sodium acetate
0.5 g of a standard platinum catalyst solution
1,330 g of an azeotropically dried toluene polyether solution that was 50% by weight toluene and 50% by weight polyether, where the polyether was an allyl initiated ethylene oxide polyether, where according to the formula in the specification R is allyl, i=7.5, and j=0; said polyether being hydroxy stopped; having the formula:

$(CH_2=CHCH_2)(OCH_2CH_2)_{7.5}OH.$

The resulting surfactant had a viscosity of 91 centistokes at 25° C.

Example 6

Surfactant B
Following the previously outlined procedure:
268 g of MDHM (mw=222) constituted the hydride fluid,
268 g of toluene solvent
0.2 g of anhydrous sodium acetate
0.5 g of a standard platinum catalyst solution
1,460 g of an azeotropically dried toluene polyether solution that was 50% by weight toluene and 50% by weight polyether, where the polyether was an allyl initiated ethylene oxide polyether, where according to the formula in the specification R is allyl, i=12.0, and j=0; said polyether being hydroxy stopped; having the formula:

$(CH_2=CHCH_2)(OCH_2CH_2)_{12}OH.$

The resulting surfactant had a viscosity of 130 centistokes at 25° C.

Example 7

Surfactant C
Following the previously outlined procedure:
142 g of $MD_4^HM$ (mw=402) constituted the hydride fluid,
142 g of toluene solvent
0.2 g of anhydrous sodium acetate
0.5 g of a standard platinum catalyst solution
1,716 g of an azeotropically dried toluene polyether solution that was 50% by weight toluene and 50% by weight polyether, where the polyether was an allyl initiated ethylene oxide polyether that was hydroxy stopped; having the formula:

$(CH_2=CHCH_2)(OCH_2CH_2)_{7.5}OH.$

The resulting surfactant had a viscosity of 530 centistokes at 25° C.

Example 8

Surfactant D
Following the previously outlined procedure:
432 g of $TD^x{}_{15}M_3^H$ (row=1,378) constituted the hydride fluid,
432 g of toluene solvent
0.2 g of anhydrous sodium acetate
0.5 g of a standard platinum catalyst solution
1,140 g of an azeotropically dried toluene polyether solution that was 50% by weight toluene and 50% by weight polyether, where the polyether was an allyl initiated ethylene oxide polyether that was hydroxy stopped; having the formula:

$(CH_2=CHCH_2)(OCH_2CH_2)_{7.5}OH.$

The resulting surfactant had a viscosity of 313 centistokes at 25° C.

In the following examples of carboxylic acid functionalized silicones, the preparative steps were as follows:

1) The surfactants were dissolved in toluene and azeotropically dried.
2) Subsequent to azeotropic drying the surfactant solution was cooled to a temperature below 100° C.
3) A small quantity of a commercial mixture of toluene and xylene sulfonic acids, hereinafter referred to by its commercial name "TX acid," was added to catalyze the reaction between the surfactant and DDSA.
4) After the acid addition, the DDSA was slowly added to the reaction mixture over the course of an hour.
5) The reaction was allowed to go to completion by holding the reaction mixture at 100° C. for five hours.
6) At the completion of the reaction, as indicated by the appearance in the infrared spectrum of the reaction mixture of bands at 1740 and 1710 cm$^{-1}$, the toluene solvent was stripped under a nitrogen purge at a reduced pressure of 10 mm Hg.

Example 9

Acid A
Following the previously outlined procedure:
350 g of surfactant A,
350 g of toluene solvent
0.5 g of TX acid
300 g of an 50 wt.% toluene 50 wt. % DDSA solution were used to prepare acid A. The resulting polyether silicone carboxylic acid had a viscosity of 1320 centistokes at 25° C.

Example 10

Acid B
Following the previously outlined procedure:
744 g of surfactant B,
744 g of toluene solvent
0.1 g of TX acid
512 g of an 50 wt.% toluene 50 wt. % DDSA solution were used to prepare acid B. The resulting polyether silicone carboxylic acid had a viscosity of 1129 centistokes at 25° C.

Example 11

Acid C
Following the previously outlined procedure:
710 g of surfactant C,
710 g of toluene solvent
0.1 g of TX acid
580 g of an 50 wt.% toluene 50 wt.% DDSA solution were used to prepare acid C. The resulting polyether silicone carboxylic acid had a viscosity of 6837 centistokes at 25° C.

Example 12

Acid D
Following the previously outlined procedure:
798 g of a surfactant, $TD^x{}_{15}M_3{}^{PE}$, surfactant D,
798 g of toluene solvent
0.1 g of TX acid
404 g of an 50 wt.% toluene 50 wt.% DDSA solution were used to prepare acid C. The resulting polyether silicone carboxylic acid had a viscosity of 1585 centistokes at 25° C.

As a carboxy or carboxylic acid functionalized polyether silicone, the acids corresponding to the surfactants were not soluble in water to any great extent. Upon neutralization the carboxy or carboxylic acid functionalized polyether silicone became water soluble.

Example 13

Personal Care Application
Solid personal care sticks were made by solubilizing and dissolving dibenzylidene sorbitol into a silicone and the polyether silicone carboxylic acid of the invention and evaluating the personal care stick for various personal care applications.

TABLE 1

| Silicone | Personal Care Sticks made with Silicones | |
|---|---|---|
| | Wt % dibenzylidene sorbitol | Stick Appearance |
| $MD^x{}_{20}D^y{}_3M$ | 2.0 | Translucent, firm |
| Acid A | 2.0 | Clear, firm |

The personal care formulations shown in Table 1 are useful as deodorant sticks, anti-perspirant sticks, lip balms, fragrance sticks, and the like. Other ingredients such as various alcohols, e.g. ethyl and lauryl, fragrances, emollients, may be dispersed into the silicone, thereby rendering the stick suitable for a particular personal care application known in the art.

Having described the invention that which is claimed is:

1. A silicone polyether carboxylic acid comprising the reaction product of:
   a) a polyether-silicone copolymer produced by a hydrosilation reaction between $A^x$ and $E^y$ $$[A^x{}_p E^y{}_q]$$

where $A^x$ represents a siloxy derivative selected from the group of silicone hydride compounds consisting of:
   i) $TD_x M_3''$
   ii) $TD_x D_y'' M_3''$
   iii) $TD_y'' M_3''$
   iv) $TD_x D_y'' M_3$
   v) $TD_y'' M_3$
   vi) $M'' D_x D_y'' M''$
   vii) $M'' D_x M''$
   viii) $MD_y'' M$
   ix) $MD_x D_y'' M$
   x) $M'' D_y'' M''$
   xi) $M'' Q$
   xii) $[D'']_z$ and any combination thereof wherein T represents a trifunctional siloxy group of the formula $RSiO_{3/2}$ with R being a saturated or unsaturated monovalent hydrocarbon radical, D represents a difunctional siloxy group of the formula $R_2SiO_{2/2}$, D" is a difunctional siloxy hydride of the formula $RHSiO_{2/2}$, M represents a monofunctional siloxy group of the formula $R_3SiO_{1/2}$ where each R is independently selected from the group of monovalent saturated or unsaturated hydrocarbon radicals; M" is a monofunctional siloxy hydride of the formula $R_2HSiO_{1/2}$, Q is a quadrifunctional siloxy group of the formula $SiO_{4/2}$; and $[D'']_z$ a cyclic oligomer of D" with z indicating the number of D" moieties forming the cyclic ring, with x greater than 1, y greater than 1 and z equal to or greater than 3 wherein p ranges from one to about 500 and q ranges from about 1 to about 500, where $E^y$ is R'(OCH$_2$CH$_2$)$_i$(OCH$_2$CH(CH$_3$))$_j$OH and where R' is an alkenyl or alkynyl group and i and j may vary from 0 to 50 such that the sum of i and j is at least one; and
   b) an acid anhydride or halide of a bi- or multi-functional organic carboxylic acid.

2. The neutralization salts of the silicone polyether carboxylic acid of claim 1.

3. The neutralization salt of claim 2 wherein the salt is a sodium salt.

4. The neutralization salt of claim 2 wherein the salt is a potassium salt.

5. The neutralization salt of claim 2 wherein the salt is an organic ammonium salt.

6. A process for making a silicone polyether carboxylic acid comprising reacting:
   a) a polyether-silicone copolymer produced by a hydrosilation reaction between $A^x$ and $E^y$ $$[A^x{}_p E^y{}_q]$$

where $A^x$ represents a siloxy derivative selected from the group of silicone hydride compounds consisting of:
   i) $TD_x M_3''$
   ii) $TD_x D_y'' M_3''$
   iii) $TD_y'' M_3''$
   iv) $TD_x D_y'' M_3$
   v) $TD_y'' M_3$
   vi) $M'' D_x D_y'' M''$
   vii) $M'' D_x M''$
   viii) $MD_y'' M$
   ix) $MD_x D_y'' M$
   x) $M'' D_y'' M''$
   xi) $M'' Q$
   xii) $[D'']_z$ and any combination thereof wherein T represents a trifunctional siloxy group of the formula $RSiO_{3/2}$ with R being a saturated or unsaturated monovalent hydrocarbon radical, D represents a difunctional siloxy group of the formula $R_2SiO_{2/2}$, D" is a difunctional siloxy hydride of the formula $RHSiO_{2/2}$, M represents a monofunctional siloxy group of the formula $R_3SiO_{1/2}$ where each R is independently selected from the group of monovalent saturated or unsaturated hydrocarbon radicals; M" is a monofunctional siloxy hydride of the formula $R_2HSiO_{1/2}$, Q is a quadrifunctional siloxy group of the formula $SiO_{4/2}$; and $[D"]_z$ a cyclic oligomer of D" with z indicating the number of D" moieties forming the cyclic ring, with x greater than 1, y greater than 1 and z equal to or greater than 3 wherein p ranges from one to about 500 and q ranges from about 1 to about 500, where $E^y$ is $$R'(OCH_2CH_2)_i(OCH_2CH(CH_3))_jOH$$

and where R' is an alkenyl or alkynyl group and i and j may vary from 0 to 50 such that the sum of i and j is at least one; and b) an acid anhydride or halide of a bi- or multi-functional organic carboxylic acid.

7. A process for making neutralization salts of a polyether silicone carboxylic acid comprising neutralizing the silicone polyether carboxylic acid of claim 6.

8. The process of claim 7 further comprising neutralizing with a sodium salt.

9. The process of claim 7 further comprising neutralizing with a potassium salt.

10. A silicone polyether carboxylic acid consisting essentially of the reaction product of:

a) a polyether-silicone copolymer produced by a hydrosilation reaction between $A^x$ and $E^y$ $$[A^x_p E^y_q]$$

where $A^x$ represents a siloxy derivative selected from the group of silicone hydride compounds consisting of:
  i) $TD_xM_3"$
  ii) $TD_xD_y"M_3"$
  iii) $TD_y"M_3"$
  iv) $TD_xD_y"M_3$
  v) $TD_y"M_3$
  vi) $M"D_xD_y"M"$
  vii) $M"D_xM"$
  viii) $MD_y"M$
  ix) $MD_xD_y"M$
  x) $M"D_y"M"$
  xi) $M"Q$
  xii) $[D"]_z$ and any combination thereof wherein T represents a trifunctional siloxy group of the formula $RSiO_{3/2}$ with R being a saturated or unsaturated monovalent hydrocarbon radical, D represents a difunctional siloxy group of the formula $R_2SiO_{2/2}$, D" is a difunctional siloxy hydride of the formula $RHSiO_{2/2}$, M represents a monofunctional siloxy group of the formula $R_3SiO_{1/2}$ where each R is independently selected from the group of monovalent saturated or unsaturated hydrocarbon radicals; M" is a monofunctional siloxy hydride of the formula $R_2HSiO_{1/2}$, Q is a quadrifunctional siloxy group of the formula $SiO_{4/2}$; and $[D"]_z$ a cyclic oligomer of D" with z indicating the number of D" moieties forming the cyclic ring, with x greater than 1, y greater than 1 and z equal to or greater than 3 wherein p ranges from one to about 500 and q ranges from about 1 to about 500, where $E^y$ is $$R'(OCH_2CH_2)_i(OCH_2CH(CH_3))_jOH$$

b) an acid anhydride or halide of a bi- or multi-functional organic carboxylic acid. and where R' is an alkenyl or alkynyl group and i and j vary from 0 to 50 such that the sum of i and j is at least one; and b) an acid anhydride or halide of a bi- or multi-functional organic carboxylic acid.

* * * * *